US00PP25467P3

(12) United States Plant Patent
Brazelton et al.

(10) Patent No.: US PP25,467 P3
(45) Date of Patent: Apr. 28, 2015

(54) BLUEBERRY PLANT NAMED 'ZF08-095'

(50) Latin Name: *Vaccinium (angustifolium×myrsinites)×corymbosum* hybrid
Varietal Denomination: ZF08-095

(71) Applicants: Fall Creek Farm and Nursery, Inc., Lowell, OR (US); Arlen Draper, Payson, AZ (US)

(72) Inventors: David M. Brazelton, Walterville, OR (US); Adam L. Wagner, Eugene, OR (US); Arlen Draper, Payson, AZ (US)

(73) Assignees: Fall Creek Farm and Nursery, Inc., Lowell, OR (US); The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/694,948

(22) Filed: Jan. 22, 2013

(65) Prior Publication Data

US 2013/0298296 P1 Nov. 7, 2013

Related U.S. Application Data

(60) Provisional application No. 61/687,971, filed on May 4, 2012.

(51) Int. Cl.
*A01H 5/00* (2006.01)

(52) U.S. Cl.
USPC ..... Plt./157

(58) Field of Classification Search
USPC ..... Plt./157
See application file for complete search history.

*Primary Examiner* — Anne Grunberg

(57) ABSTRACT

The new blueberry plant variety 'ZF08-095' is provided. 'ZF08-095' is an ornamental variety intended for nursery, landscape, and home garden use. The variety is a semi-dwarf with a round shape and shiny dark green leaves that turn shades of red, purple and yellow in the fall. 'ZF08-095' has attractive fruit that ripens from red to black in mid to late July, and has a mild, sweet flavor.

4 Drawing Sheets

Latin name of the family, genus, and species:
Family—Ericaceae.
Genus—*Vaccinium.*
Species—(*angustifolium×myrsinites*)×*corymbosum* hybrid.

Variety denomination: The new blueberry plant claimed is of the variety denominated 'ZF08-095'.

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of ornamental blueberry (*Vaccinium* (*angustifolium×myrsinites*)×*corymbosum* hybrid) and referred to as 'ZF08-095', as herein described and illustrated.

The new blueberry plant variety 'ZF08-095' was selected in Lowell, Oreg. in 2008. 'ZF08-095' is an ornamental variety intended for nursery, landscape, and home garden use. The variety is a semi-dwarf with a round shape and shiny dark green leaves that turn shades of purple, red, and yellow in the fall. 'ZF08-095' has attractive fruit that ripens from red to black in mid to late July, and has a mild, sweet flavor.

Pedigree and History: The new blueberry plant originated from a 1988 controlled cross pollination of 'JU 60' (female parent, unpatented) by 'US 702' (pollen parent, unpatented). 'ZF08-095' was selected from a seedling population grown in Oregon from seed obtained from the Fruit Laboratory, USDA-ARS, Beltsville, Md. The cross that produced the seed, which was made in 1988, involved three tetraploid species of *Vaccinium*: (*V. myrsinites×V. angustifolium*)×[*V. corymbosum*×(*V. myrsinites×V. angustifolium*)]. The seedling was first selected from a high density field planting in the summer of 2008. 'ZF08-095' was propagated using traditional techniques and has been planted in replicated trials since 2009. The original trial plot was removed in 2011, and all subsequent observations have been collected on a second plot established in 2010. 'ZF08-095' has been observed in plots of 2-3 plants in 2009, 2010, 2011, and 2012. In comparison to the female parent, 'JU-60', 'ZF08-095' has a leaf covered with less wax, giving ZF08-95 a more shiny appearance to the leaves. In comparison to the pollen parent, 'US-702', 'ZF08-095' has a much shorter plant height, smaller leaves, and shorter internode spacing.

The new variety can be compared to ornamental variety 'Burgundy' in that 'ZF08-095' has smaller, darker colored, shiny leaves, and larger berries that are darker in color.

The new variety can be compared to ornamental variety 'Sunshine Blue' in that 'ZF08-095' has darker fruit and smaller, shiny, dark green leaves as well as a more compact growing habit.

The new blueberry plant variety 'ZF08-095' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'ZF08-095' has not been observed under all possible environmental conditions. The phenotype may vary somewhat with variations in environment and cultural practices such as temperature and light intensity without, however, any variance in genotype.

The following traits have been repeatedly observed in Lowell, Oreg., and are determined to be the unique characteristics of the new blueberry plant variety 'ZF08-095':

1. Uniform, round shape.
2. Dark blue to black fruit
3. Shiny leaves
4. Red, yellow, and dark purple fall foliage.

BRIEF DESCRIPTION OF THE DRAWINGS

The accompanying photographic illustration shows typical specimens in full color of the foliage and fruit of the new variety 'ZF08-095'. The colors are as nearly true as is reasonably possible in a color representation of this type.

BOTANICAL DESCRIPTION

Figure 1:
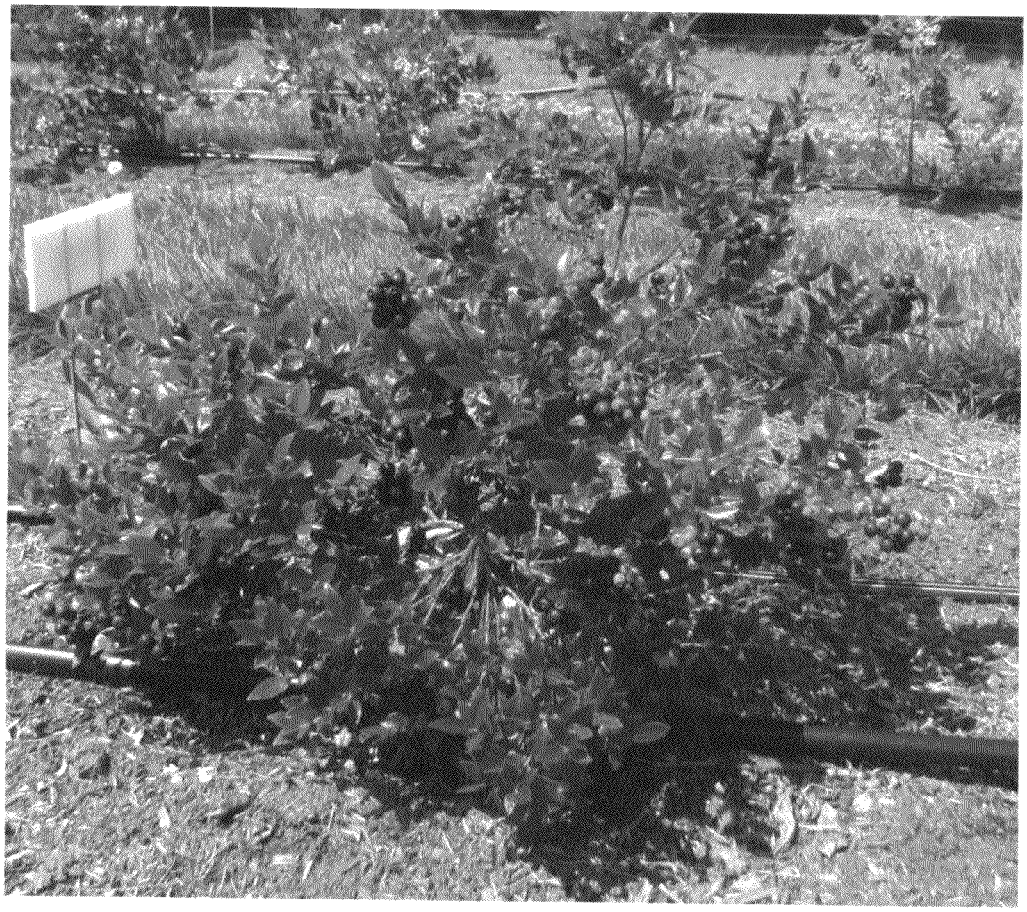
FIG. 1 is a photograph of the new variety 'ZF08-095', highlighting the plant's uniform, round growth habit and shiny leaves.
Figure 2:
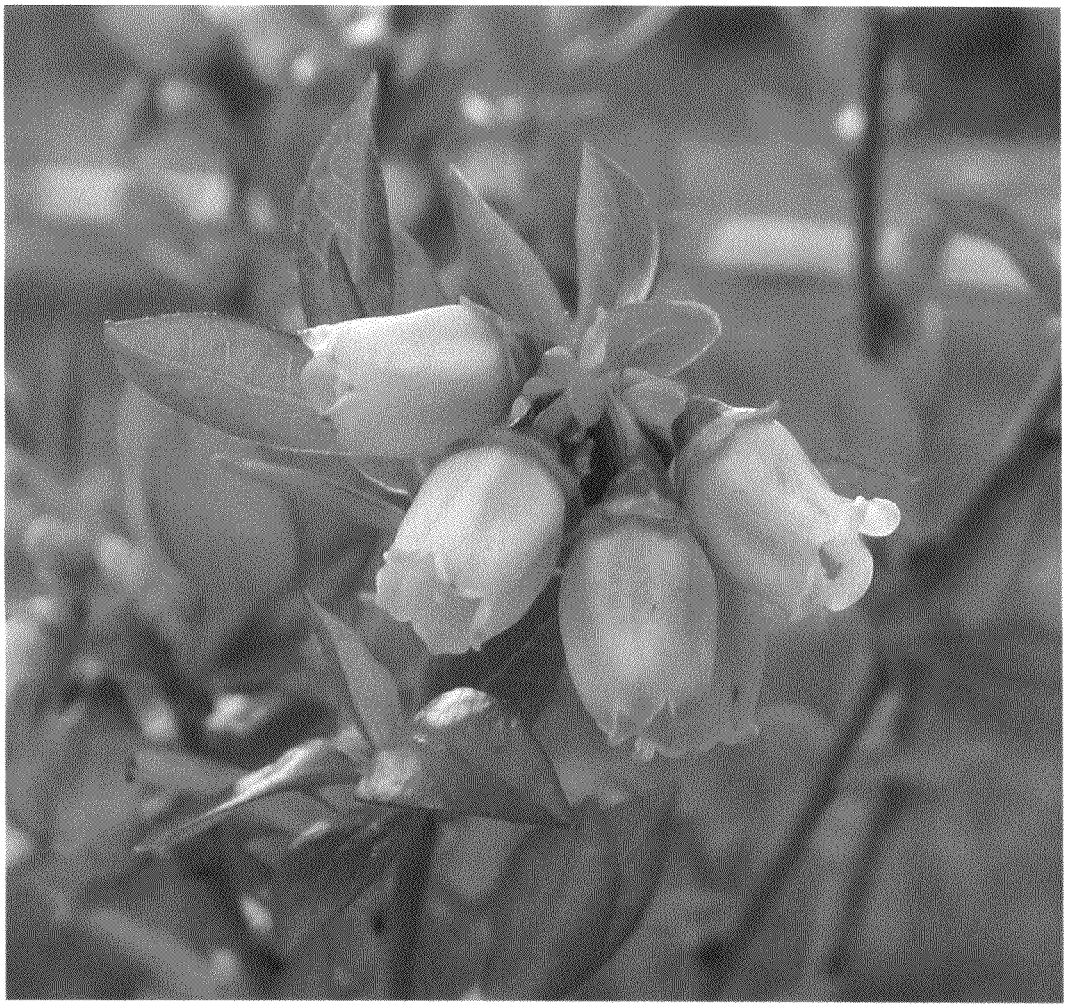
FIG. 2 is a photograph of the flowers of the new variety 'ZF08-095'.
Figure 3:
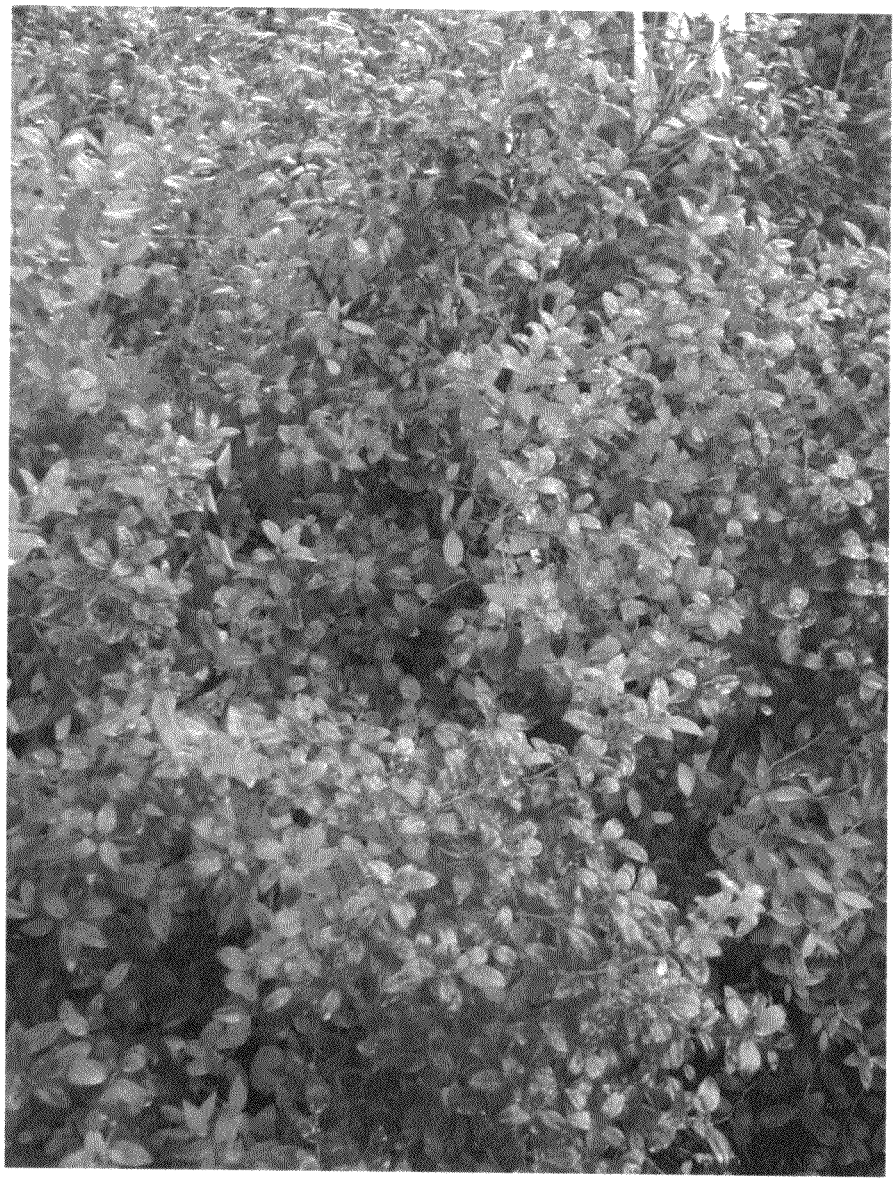
FIG. 3 is a photograph of the red, yellow, and purple fall coloring of the new variety 'ZF08-095'.
Figure 4:
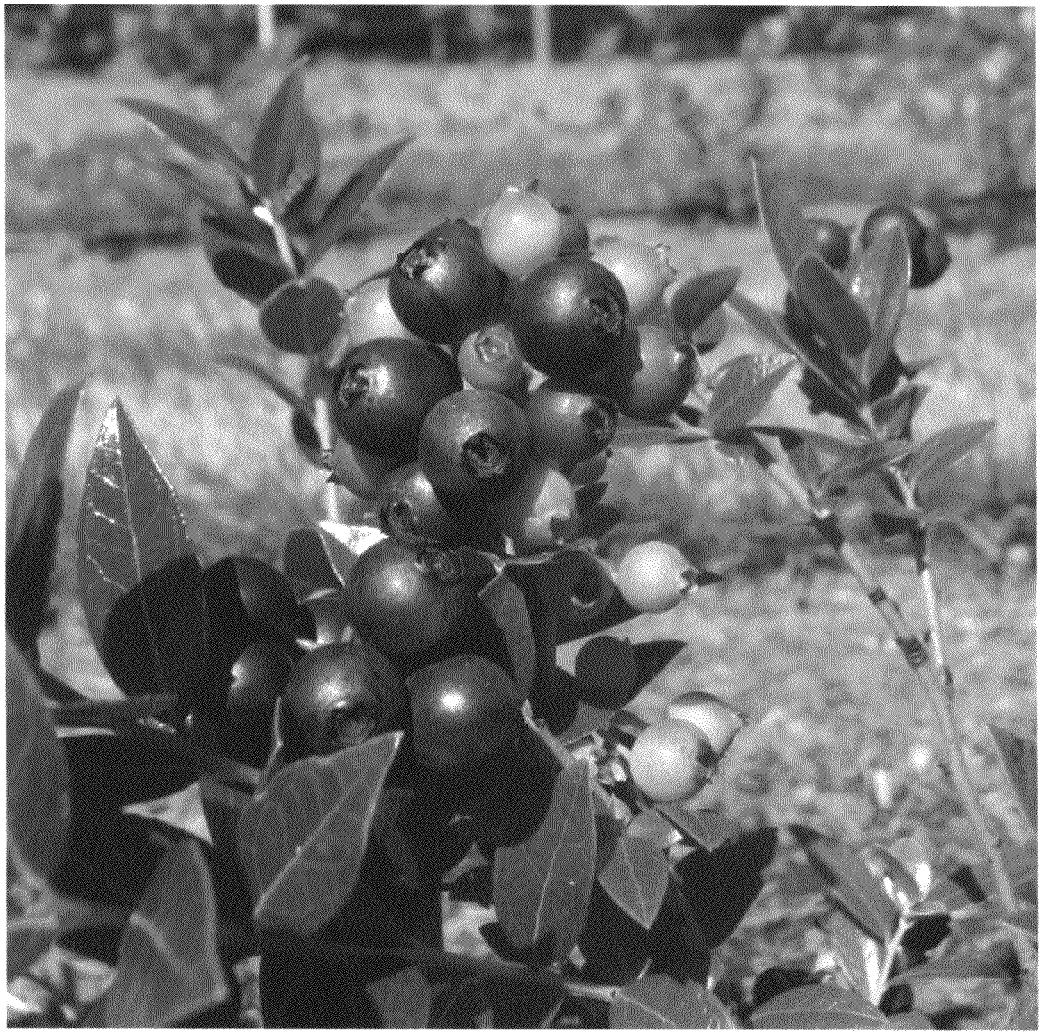
FIG. 4 is a photograph of the fruit of the new variety 'ZF08-095'.

The following detailed description sets forth the distinctive characteristics of 'ZF08-095'. The data which defines these characteristics was collected from asexual reproductions of the original selection. Dimensions, sizes, colors and other characteristics are approximations and averages set forth as accurately as possible. The plant history was taken on plants that were three and four years old, and the descriptions relate to plants grown in the field in Lowell, Oreg. Color designations are from "The Pantone Book of Color" (by Leatrice Eiseman and Lawrence Herbert; Harry N. Abrams, Inc., Publishers, New York, 1990). Where the Pantone color designations differ from the colors in the photographs, the Pantone colors are accurate.

Classification:

*a. Family*.—Ericaceae.
*b. Genus*.—*Vaccinium*.
*c. Species*.—(*angustifolium*×*myrsinites*)×*corymbosum* hybrid.
*d. Common name*.—Blueberry.

Parentage:

*Female parent*.—'JU 60' (unpatented).
*Male parent*.—'US 702' (unpatented).

Market class: 'ZF08-095' is an ornamental variety intended for nursery, landscape, and home garden use.

PLANT

Height of plant: 2 year old plants average 14-18".
Canopy diameter: 2 year old plants average 14-18".
Growth habit: Round.
Plant vigor : Moderate.
Twigginess : Moderate.
Suckering: Low.
Evergreenness: Semi evergreen in Oreg.
Chilling requirement: Approximately 500 hours.
Cold hardiness: Based on pedigree, estimated USDA hardiness zones 7-8.
Productivity: In Lowell, Oreg., per plant harvest weight on 2 year old plants — 0.84 lbs.
Propagation: Easy to propagate from softwood cuttings.
Disease resistance/susceptibility:

*a. Root rot* (*Phytophthora cinnamomi*).—Does not appear to be overly susceptible.
*b. Stem blight* (*Botryosphaeria spp*).—Undetermined.
*c. Phomopsis twig blight* (*Phomopsis vaccinii*).—Susceptible to *Phomopsis* twig blight.
*d. Botryosphaeria stem canker* (*Botryosphaeria corticis*).—Undetermined.
*e. Bacterial cane canker* (*Pseudomonas syringae*).—Susceptible to bacterial cane canker (*Pseudomonas syringae*).
*f. Botrytis blight* (*Botrytis cinerea*).—Does not appear to be overly susceptible.
*g. Leaf spot* (*Septoria spp*.).—Does not appear to be overly susceptible.
*h. Leaf rust* (*Naohidemyces vaccinii*).—Does not appear to be overly susceptible.
*i. Bud mites* (*Acalatus vaccinii*).—Undetermined.

Survival: Survival in field plots is moderate.

TRUNK AND BRANCHES

Texture:

*a. Surface texture new wood*.—Smooth.
*b. Surface texture* 1 *year wood*.—Smooth.
*c. Surface texture* 3 *year wood*.—Rough.

Color:

*a. Color new wood*.—Pantone Green Oasis 15-0538.
*b. Color rough bark* 1 *year*.—Pantone colors Raw Umber 17-1422, Green Oasis 15-0538, and Baked Apple 18-1648.
*c. Color rough bark* 3 *year*.—Pantone colors Raw Umber 17-1422, Sand 15-1225, and Cork 16-1422.

FOLIAGE

Internode length: Average 7.69 mm.
Leaf dimensions:

*a. Leaf length*.—Average 34.15 mm.
*b. Leaf width*.—Average 16.11 mm.

Leaf shape: Elliptical with acute apex and rounded to semi rounded base.
Leaf margin: Finely serrate; serrations not always present.
Leaf color:

*a. Leaf color upper leaf surface*.—Pantone Chive 19-0323.
*b. Leaf color lower leaf surface*.—Pantone Bluish Olive 18-0316.
*c. Fall foliage color*.—Pantone colors Holly Berry 17-1633, Claret Red 17-1740, Maroon 18-1619, Lemon Drop 12-0736, Chive 19-0323, Peridot 17-0336.

Pubescence:

*a. Pubescence upper leaf surface*.—Absent.
*b. Pubescence lower leaf surface*.—Absent.
*c. Pubescence leaf margins*.—Absent.

Petiole:

*a. Petiole length*.—Average 1.23 mm.

*b. Petiole color*.—Pantone color Green Oasis 15-0538.

*c. Petiole surface texture*.—Smooth.

Leafing vs flowering: Flower bud break occurs prior to or with vegetative bud break. Flowers persist through initial vegetative growth period.

FLOWERS

Flower arrangement: Flower clusters arranged alternately along branch.

Fragrance: Mild, sweet fragrance.

Anther:

*a. Anther length*.—Average 2.95 mm.

*b. Anther color*.—Pantone colors Autumn leaf 17-1347 and Sierra 18-1239.

Immature flower color: Pantone colors White Smoke 12-0704 & Rapture Rose 17-1929.

Pedicel:

*a. Pedicel length flower*.—Average 3.36 mm.

*b. Pedicel color*.—Pantone color Apple Green 15-0543.

Peduncle:

*a. Peduncle length flower*.—Variable, average 6.75 mm.

*b. Peduncle color*.—Pantone color Apple Green 15-0543.

Flower shape: Cylindrical.

Pollen:

*a. Pollen staining*.—Staining with 2% acetocarmine: 95%.

*b. Pollen abundance*.—Medium.

*c. Pollen color*.—Pantone color Pale Banana 12-0824.

Flower length: Average of 7.39 mm.

Corolla:

*a. Corolla length*.—Average 5.0 mm.

*b. Corolla diameter*.—Average 4.38 mm.

*c. Corolla color*.—Snow White 11-0602 & White Swan 12-0000.

*d. Corolla texture*.—Smooth.

*e. Corolla aperture*.—Average of 3.1 mm.

Style length: Average of 5.02 mm.

Calyx:

*a. Calyx diameter*.—Average 3.36 mm.

*b. Calyx surface*.—Smooth.

*c. Calyx color*.—Pantone color Apple green 15-0543.

Pistil color: Pantone color Apple Green 15-0543.

Flowering period: Late April through late May in Lowell, Oreg.

Flowering cluster: Loose.

Number of flowers: Average 8 flowers per cluster.

Stigma location: Average 0.45 mm below lip of corolla.

Self-compatibility: Low. 35% of self-pollinated flowers reach maturity.

FRUIT

Mean harvest date: ZF08-095 is an ornamental variety, not intended for commercial harvest.

Mean date last pick: ZF08-095 is an ornamental variety, not intended for commercial harvest.

Fruit ripening: Fruit begins turning green to red in late June, first ripe fruit is seen in early July, and 50% ripe occurs in mid-July in Lowell, Oreg.

Calyx:

*a. Calyx aperture*.—Average 3.6 mm.

*b. Calyx lobes*.—Indistinct.

*c. Calyx depth*.—Average 0.38 mm.

Berry cluster: Loose.

Berry pedicel:

*a. Length*.—Average 4.98 mm.

*b. Surface texture*.—Smooth.

Berry peduncle:

*a. Length*.—Average 4.51 mm.

*b. Surface texture*.—Smooth.

Berries per cluster: Average 6-8 berries per cluster.

Berry detachment: Easy.

Berry weight: Average 0.5 g.

Berry height: Average 9.02 mm.

Berry width: Average 9.77 mm.

Berry shape: Round.

Berry color:

*a. Immature berry color*.—Pantone color Mellow Green 12-0426, Claret Red 17-1740 and True Red 19-1664.

*b. Berry skin color on plant*.—Pantone color Shale 19-3903 to Dark Navy 19-4013.

*c. Berry skin color after harvest*.—Pantone color Shale 19-3903.

*d. Berry skin color after polishing*.—Pantone color Jet Black 19-0303.

Berry wax: Low.

Berry flesh color: Pantone color White Swan 12-0000.

Pedicel scar: Average 1.12 mm.

Berry firmness: Medium.

Berry flavor: Mild, sweet.

Berry texture: Smooth.

SEEDS

Seed color: Pantone color Fudgesickle 19-1431.

Seed length: Average 1.63 mm.

Seed width: Average 1.0 mm.

Seed weight: Average 0.35 mg.

Seeds per berry: Average 14.

The invention claimed is:

1. A new and distinct variety of blueberry plant named 'ZF08-095', substantially as illustrated and described herein.

* * * * *